(12) United States Patent
Sutton

(10) Patent No.: US 7,608,041 B2
(45) Date of Patent: Oct. 27, 2009

(54) MONITORING AND CONTROL OF SLEEP CYCLES

(76) Inventor: William R. Sutton, 4898 Delores Dr., Pleasanton, CA (US) 94566

( * ) Notice: Subject to any disclaimer, the term of this patent is extended or adjusted under 35 U.S.C. 154(b) by 0 days.

(21) Appl. No.: 11/788,438

(22) Filed: Apr. 20, 2007

(65) Prior Publication Data

US 2007/0287930 A1    Dec. 13, 2007

Related U.S. Application Data

(63) Continuation of application No. 10/849,080, filed on May 18, 2004, now abandoned.

(60) Provisional application No. 60/471,897, filed on May 19, 2003.

(51) Int. Cl.
  *A61B 5/00*    (2006.01)
(52) U.S. Cl. .................................................... 600/300
(58) Field of Classification Search ........................ None
  See application file for complete search history.

(56) References Cited

U.S. PATENT DOCUMENTS

| 5,101,831 | A | * | 4/1992 | Koyama et al. | 600/500 |
| 5,928,133 | A | * | 7/1999 | Halyak | 600/26 |
| 6,547,728 | B1 | * | 4/2003 | Cornuejols | 600/300 |
| 6,888,779 | B2 | * | 5/2005 | Mollicone et al. | 368/10 |

* cited by examiner

*Primary Examiner*—Robert L Nasser
(74) *Attorney, Agent, or Firm*—Berkeley Law & Technology Group, LLP

(57) ABSTRACT

A system is provided including: a monitor for monitoring a user's sleep cycles; a processor which counts the sleep cycles to provide a sleep cycle count and which selects an awakening time according to a decision algorithm including the sleep cycle count as an input; and an alarm for awakening the user at the awakening time. Use of the sleep cycle count as an input to the decision algorithm advantageously enables a user to more fully control and optimize his or her personal sleeping behavior.

27 Claims, 3 Drawing Sheets

MONITORING AND CONTROL OF SLEEP CYCLES

CROSS REFERENCE TO RELATED APPLICATIONS

This application is a continuation of Ser. No. 10/849,080, filed May 18, 2004 now abandoned which in turn claims priority to provisional application 60/471,897, filed on May 19, 2003, both applications are hereby incorporated by reference in their entirety.

FIELD OF THE INVENTION

The present invention relates to monitoring and controlling sleep.

BACKGROUND

During sleep, humans usually pass through five stages or phases of sleep: stages 1, 2, 3, 4, and REM (rapid eye movement) sleep, then the cycle starts over again with stage 1. For adults, typically almost 50 percent of total sleep time is stage 2 sleep, about 20 percent is REM sleep, and the remaining 30 percent is stage 1, 3, and/or 4 sleep. Infants, by contrast, spend about half of their sleep time in REM sleep.

Stage 1 sleep is light sleep. A person in stage 1 sleep drifts in and out of sleep and can be awakened easily. Eye movement and muscle activity are slow. People awakened from stage 1 sleep often remember fragmented visual images. Many also experience sudden muscle contractions called hypnic myoclonia, often preceded by a sensation of starting to fall.

These sudden movements are similar to the "jump" people make when startled. During stage 2 sleep, eye movements stop and brain waves (fluctuations of electrical activity that can be measured by electrodes) become slower, with occasional bursts of rapid waves called sleep spindles. In stage 3 sleep, extremely slow brain waves called delta waves begin to appear, interspersed with smaller, faster waves. By stage 4, the brain produces delta waves almost exclusively. It is very difficult to wake someone during stages 3 and 4, which together are called deep sleep. There is no eye movement or muscle activity during stage 3 or 4 sleep. People awakened during deep sleep do not adjust immediately and often feel groggy and disoriented for several minutes after they wake up. During REM sleep, breathing becomes more rapid, irregular, and shallow, significant eye movement occurs, heart rate and blood pressure increase, and limb muscles become temporarily paralyzed. When people awaken during REM sleep, they often describe bizarre and illogical tales (i.e., dreams).

The first REM sleep period usually occurs about 70 to 90 minutes after the beginning of a night's sleep. A complete sleep cycle takes 90 to 110 minutes on average. The first sleep cycles each night contain relatively short REM periods and long periods of deep sleep. As the night progresses, REM sleep periods increase in length while deep sleep periods decrease in length. By morning, people spend nearly all their sleep time in stages 1, 2, and REM.

People lose some of the ability to regulate their body temperature during REM, so abnormally hot or cold temperatures in the environment can disrupt this stage of sleep. If a person's REM sleep is disrupted one night, the normal sleep cycle progression is often not followed the next night. Instead, such a person often slips directly into REM sleep and goes through extended periods of REM sleep to "catch up" on this stage of sleep.

Circadian rhythms are regular changes in mental and physical characteristics that occur in the course of a day. Most circadian rhythms are controlled by the body's biological "clock." This clock, called the suprachiasmatic nucleus (SCN) is actually a pair of pinhead-sized brain structures that together contain about 20,000 neurons. The SCN rests in a part of the brain called the hypothalamus, just above the point where the optic nerves cross. Light that reaches photoreceptors in the retina creates signals that travel along the optic nerve to the SCN.

Signals from the SCN travel to several brain regions, including the pineal gland, which responds to light-induced signals by switching off production of the hormone melatonin. The body's level of melatonin normally increases after darkness falls, making people feel drowsy. The SCN also governs functions that are synchronized with the sleep/wake cycle, including body temperature, hormone secretion, urine production, and changes in blood pressure.

From experiments where people are deprived of light and other external time cues, it is apparent that most people's biological clocks work on a 25-hour cycle rather than a 24-hour one. But because sunlight or other bright lights can reset the SCN, human biological cycles normally follow the 24-hour cycle of the sun, rather than the innate 25-hour cycle. Circadian rhythms can be affected to some degree by almost any kind of external time cue, such as the beeping of an alarm clock, the clatter of a garbage truck, or the timing of meals.

When travelers pass from one time zone to another, they suffer from disrupted circadian rhythms, an uncomfortable feeling known as jet lag. For instance, a person traveling from California to New York will "lose" 3 hours according to his or her biological clock. Such a traveler will feel tired when the alarm rings at 8 AM the next morning because it is still 5 AM according to the traveler's biological clock. It usually takes several days for a traveler's body cycles to adjust to the new time.

To reduce the effects of jet lag, the biological clock can be manipulated with a technique called light therapy. People are exposed to special lights, many times brighter than ordinary household light, for several hours near the time the subjects want to wake up. This helps them reset their biological clocks and adjust to a new time zone. See a book entitled "Promise of Sleep" by Dr. William Dement (pgs. 92-96, 408).

Although insufficient sleep is a common problem, there is also research that shows that people that sleep more than 8 hours a day have a higher mortality rate than those that sleep less than 8 hours. Further studies show that a healthy range for a night's sleep can be as short as 4 hours for some individuals. While people typically think they are tired because of insufficient sleep, people may in fact be tired or shortening their lives because of too much sleep. See for instance, "Mortality Risk Associated with Sleeping Patterns of Adults" by Deborah L Wingard and Lisa F Berkman in the Feb. 15, 2002 issue of the Archives of General Psychiatry.

As indicated above, human sleeping behavior is complex, and a disruption of a normal sleeping pattern (as in jet lag), or an undiagnosed abnormal sleeping pattern, can have significant adverse health and/or performance consequences. For this reason, methods for monitoring sleep to account for the difference between various stages of the sleep cycle have been considered in the art. For example, U.S. Pat. No. 4,228,806 considers an alarm clock having a monitor to determine whether a user is in a deep sleep stage or not. An alarm interval is set, and the alarm sounds at the first time during the interval when the user is not in a deep sleep stage or at the end of the interval if the user is in deep sleep throughout the interval. Similarly, US patent application publication 2002/0080035 considers an alarm clock having an alarm that is automatically adjusted to account for a user's sleep stage at the time of awakening (e.g., a relatively loud alarm is sounded if the user is in deep sleep, and a relatively soft alarm is sounded if the user is in light sleep).

However, these methods do not enable a user to fully optimize and control his or her sleep cycles to improve health and/or performance. Thus, there is an unmet need in the art for such methods and systems.

SUMMARY

A system according to an embodiment of the invention includes a monitor for monitoring a user's sleep cycles, a processor which counts the sleep cycles to provide a sleep cycle count and which selects an awakening time according to a decision algorithm including the sleep cycle count as an input, and an alarm for awakening the user at the awakening time. Use of the sleep cycle count as an input to the decision algorithm advantageously enables a user to more fully control and optimize his or her personal sleeping behavior.

DETAILED DESCRIPTION

Figure 1:
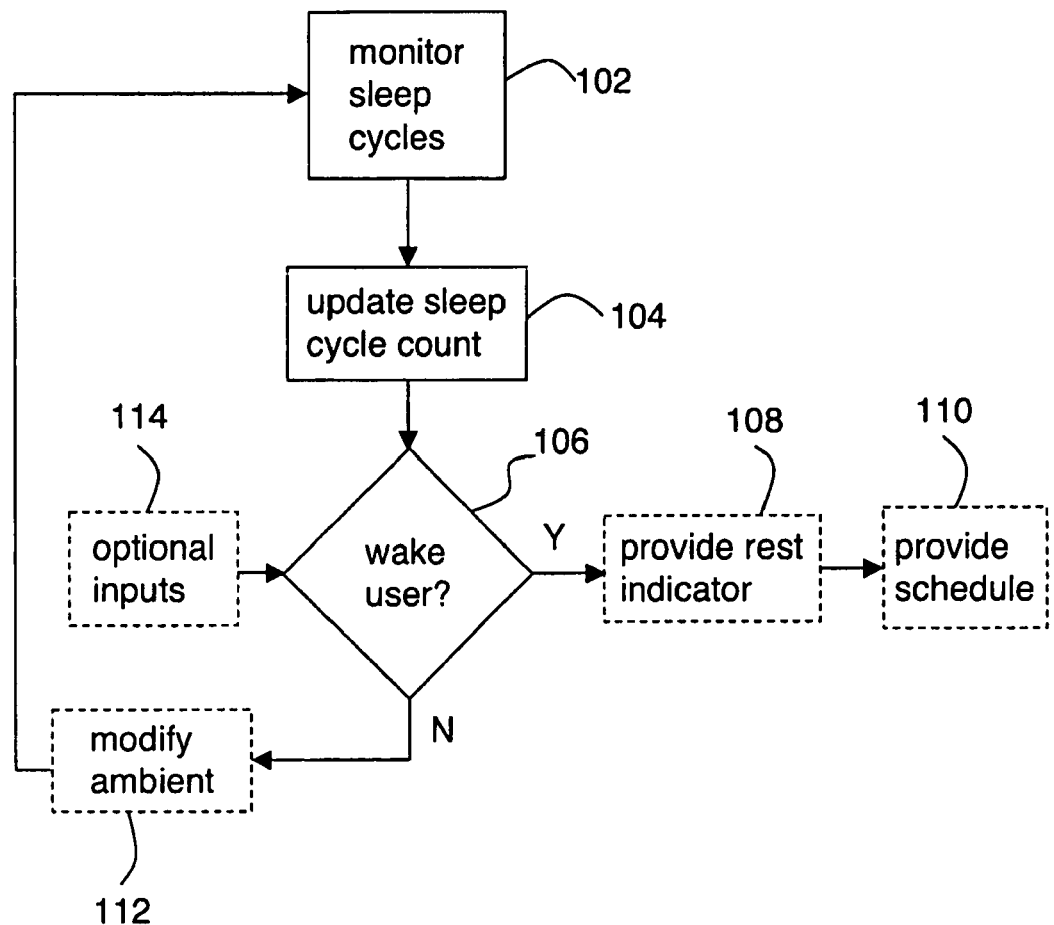
FIG. 1 is a flow diagram of a sleep control method according to an embodiment of the invention.

FIG. 1 is a flow diagram of a sleep control method according to an embodiment of the invention. On FIG. 1, a user's sleep cycles are monitored (102). By monitoring the sleep cycles, a sleep cycle count is updated (104). Typically, completion of a REM sleep stage is regarded as completion of a sleep cycle, although any other stage of sleep could also be used for this purpose. A decision algorithm 106 is used to determine whether or not to wake the user. Decision algorithm 106 includes the sleep cycle count obtained by monitoring the user's sleep cycles as an input. Decision algorithm 106 can also include optional inputs 114. If a decision is made not to awaken the user responsive to a particular input or set of inputs, then monitoring continues (102). Optionally, the ambient environment of the sleeping user can be altered (112). If a decision is made to awaken a user responsive to a particular input or set of inputs, then optionally an indication of whether or not sufficient rest has been obtained (108) and/or a schedule of events (110) can be provided to the user.

Rest indication 108 can be provided based on a comparison of monitored sleep cycle data recorded during the previous night with nominal sleep cycle data. Preferably, such nominal sleep cycle data is obtained by consistently recording sleep cycle data for the user, and combining the recorded data with user feedback indicating daily fatigue level, daily energy level and/or performance. Such user feedback can be stored once input, so that reentry of user feedback is not required. Rest indication 108 can be of particular value to users who are pilots, drivers, doctors, or who work in other professions making stringent demands on alertness.

The method of FIG. 1 can include optional ambient modification 112, which can be used to modify a user's sleep cycles in accordance with a user's desires. Effective methods for ambient modification 112 include, but are not limited to, altering a temperature (of a room and/or of an electric blanket), altering a light level, and altering a sound level. Typically, a user would experiment with a particular ambient modification (e.g., ambient temperature during various sleep stages), and correlate the ambient modification with feedback information such as consistency and quality of recorded sleep cycles and/or energy level and performance during the following day. In this manner, a user can determine, in a personalized manner, what ambient modification (if any) is most suitable.

Discussion of provision of a schedule 110 to the user will be discussed below in connection with Example 2.

Figure 2:
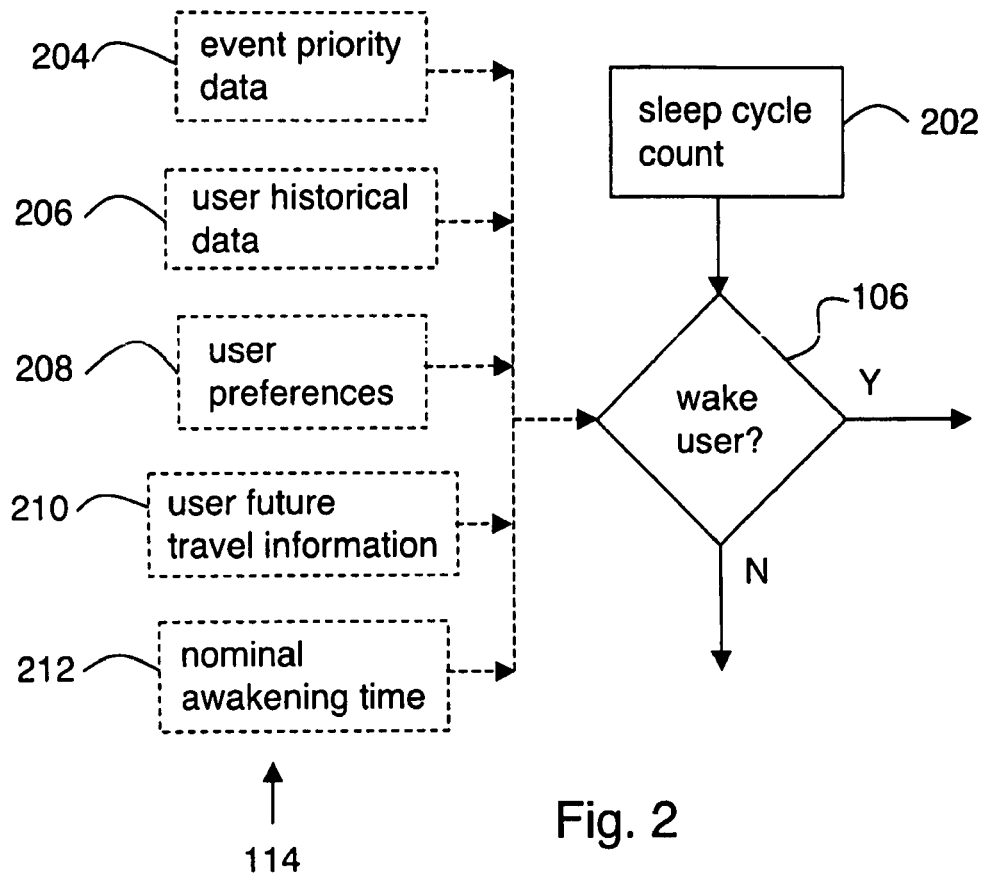
FIG. 2 is a flow diagram showing optional decision inputs for the embodiment of FIG. 1.

One mode of operation of the method of FIG. 1 is to awaken the user after a certain number of sleep cycles have been completed. Various modifications and elaborations of this mode of operation can be provided by making use of optional inputs 114 on FIG. 1 and by appropriately modifying decision algorithm 106. FIG. 2 is a flow diagram showing various exemplary optional inputs 114 to decision algorithm 106 of FIG. 1. For example, a nominal awakening time 212 can be provided to decision algorithm 106 and the user can be awakened either at the nominal awakening time or at the completion of a set number of sleep cycles, whichever occurs earlier. User preferences 208, such as desired number of sleep cycles, and preferred phase of a sleep cycle to be awakened in can be included as optional inputs to decision algorithm 106. Preferences 208 can include parameters and/or rule-based information for resolving possibly conflicting directives.

For example, the desired number of sleep cycles can conflict with the nominal awakening time, and this conflict can be resolved in various ways which the user can select via preferences 208. Ways of resolving this conflict include giving priority to the nominal awakening time (as in the above example), giving priority to the desired number of sleep cycles, or allowing completion of the desired number of sleep cycles if an estimated sleep cycle completion time is "close" to the nominal awakening time (i.e., later than the nominal awakening time by no more than a user-selectable time margin).

User historical data 206 can be included as an optional input 114 to decision algorithm 106. Such historical data can include past information on nightly sleep cycles, for review by the user and/or for use in providing estimates in decision algorithm 106. For example, historical data 206 can be used to refine assumed sleep cycle phase durations to provide more accurate and personalized data for the user.

User future travel information 210 and event priority data 204 will be discussed in connection with Examples 1 and 2 below respectively.

Figure 3:
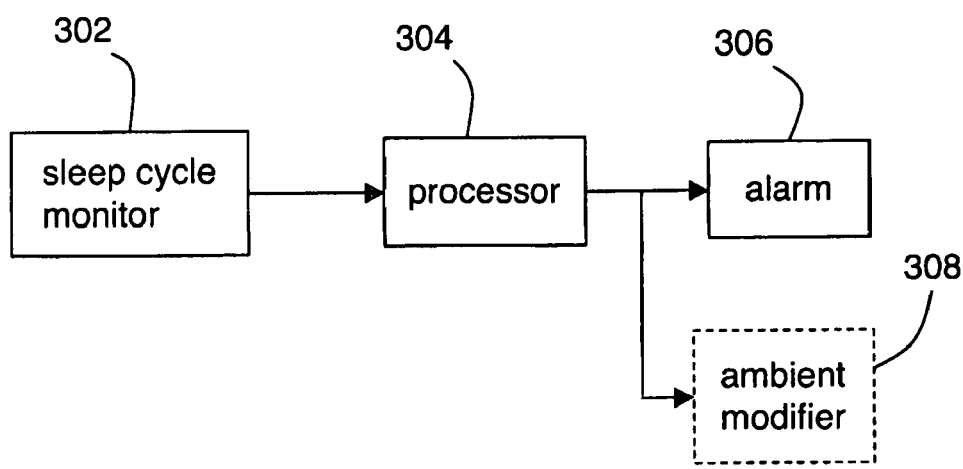
FIG. 3 is a block diagram of a sleep control system according to an embodiment of the invention.

FIG. 3 shows a block diagram of a system according to an embodiment of the invention. A sleep cycle monitor 302 provides sleep cycle input to a processor 304. Processor 304 is connected to an alarm 306, and may also be connected to an optional ambient modifier 308.

Monitor 302 monitors signals from the user's body. The monitored signals are signals related to sleep cycles (e.g., electrical brain waves, body movement, heart rate, body temperature and/or breathing rate). Suitable physiological signals to use in such monitoring are known in the art, as are methods for analyzing such signals to provide information on a user's sleep state and to derive a sleep cycle count. Monitored signals are typically picked up via electrodes or sensors in contact with or near the user's body. Electrodes can be active or passive, and are widely available in the art. Preferably, the number of electrodes or sensors is no more than what is required to provide suitable sleep cycle information. Preferably, monitor 302 is non-invasive, such that the electrodes and/or sensors used to pick up signals are easy to position and remove.

Examples of suitable electrodes and/or sensors include: a headband with electrodes placed inside the headband, electrodes attached to the face or forehead, sleeves placed over the fingers, wrist bands with electrodes under the band, sensors in the sheets or mattress (e.g., as in U.S. Pat. Nos. 6,485,441 and 6,468,234), strain gauges across the user's chest, motion sensors, or any combination thereof. Furthermore, any method can be used to transmit signals from the electrodes or sensors of monitor 302 to monitor 302 (or to processor 304), including wired transmission and wireless transmission.

Processor 304 on FIG. 3 implements decision algorithm 106 of FIG. 1. Such implementation can be in hardware and/or in software. Preferably, decision algorithm 106 is implemented as software running on a general-purpose personal computer, since such implementation provides the convenient user interface of the computer and allows easy selection, modification and/or updating of the decision algorithm by input to (or modification of) the software.

Alarm 306 on FIG. 3 can be any device suitable for waking up a user. Such devices include, but are not limited to, audible alarms and/or visible lights. Furthermore, alarm 306 can be a progressive alarm which gradually provides a more intense stimulus and/or changes the kind of stimulus (e.g., from a music broadcast to a buzzer) to a user until the user awakes.

Optional ambient modifier 308 on FIG. 3 can include devices for altering an ambient temperature (of a room and/or of an electric blanket), altering an ambient light level, and/or altering an ambient sound level.

Figure 4:
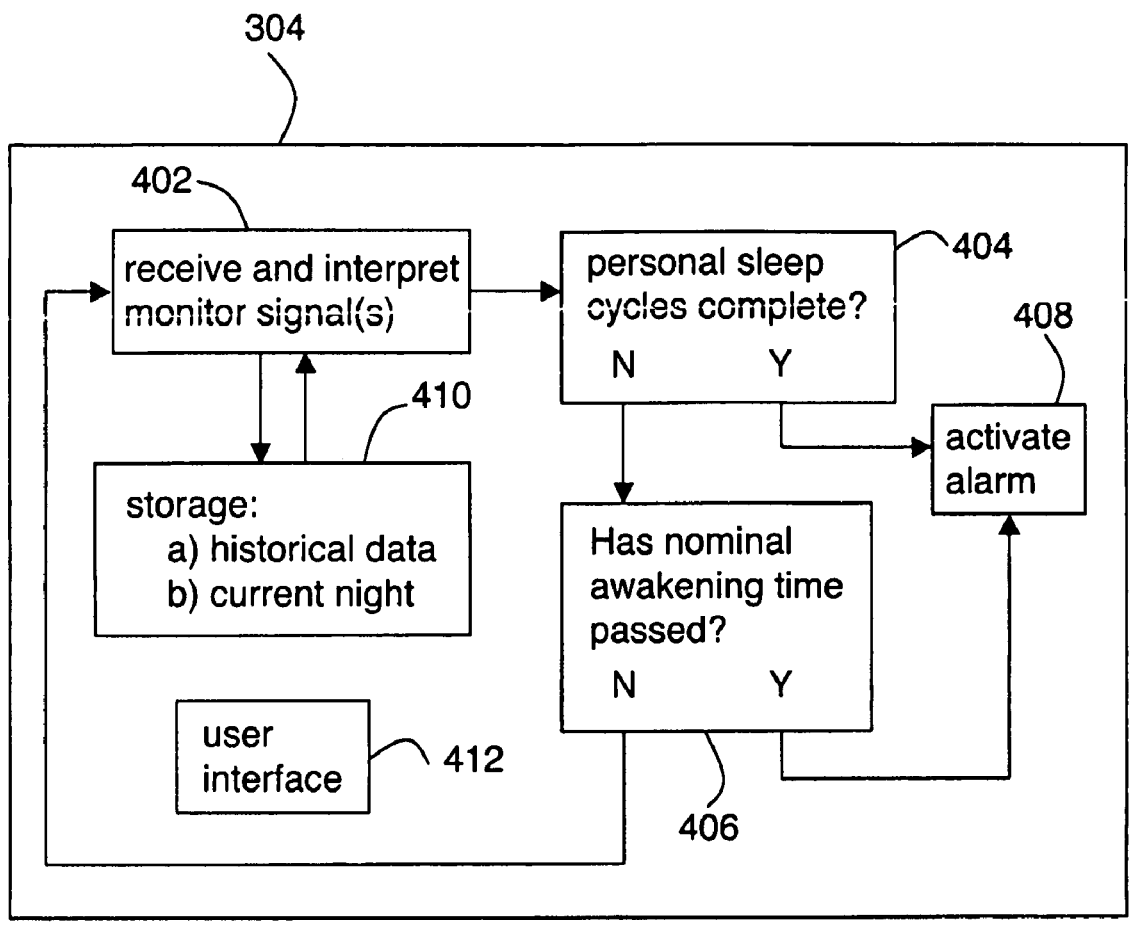
FIG. 4 shows an operation diagram of an exemplary processor 304 in the embodiment of FIG. 3.

FIG. 4 shows an operation diagram of an exemplary processor 304 in the embodiment of FIG. 3. On FIG. 4, processor 304 receives and interprets (402) monitor signals. The sleep cycle count is updated responsive to interpreted monitor signals. Furthermore, monitor signals for the current night are recorded in storage 410. Storage 410 preferably also includes historical data from earlier nights. In the example of FIG. 4, it is assumed the desired decision algorithm (i.e., 106 on FIG. 1) is to awaken the user after completion of a desired number of personal sleep cycles, or at a nominal awakening time, whichever is earlier. Blocks 404 and 406 on FIG. 4 show implementation of this logic for triggering alarm activation (408). A user interface 412 is provided to enable a user to provide input to the system and to receive output from the system.

More detailed and specific modes of operation of embodiments of the invention are discussed in connection with the following two examples.

EXAMPLE 1

The user is assumed to be an athlete that has used a system according to an embodiment of the invention for sufficient time to collect useful historical data and who will be competing in an event in a foreign time zone. For the purposes of this example, the athlete is living and training in California for an event in England, and desires to slowly adjust to the new time zone before he travels overseas.

One week before departing to England, the athlete, who ordinarily gets up at 8:00 AM, sets his system up for 8:00 AM London time. The system calculates the time difference to be 8 hours. The system will not attempt to make the full 8 hour adjustment over 7 days, but only a more reasonable three hours adjustment. Otherwise the athlete would be going to bed in daylight hours during the week prior to the event. This would not be practical. Over the next 7 days the system turns on a light at a low level a half hour earlier on each successive morning and slowly ramps up to full intensity over the subsequent half hour after the light is turned on. The following table represents this schedule:

|     | Day |     |     |     |     |     |     |
| --- | --- | --- | --- | --- | --- | --- | --- |
|     | M | T | W | T | F | S | S |
| Set | 8 AM | 7:30 | 7 | 6:30 | 6 | 5:30 | 5 AM |

Thus, in this example, a system according to the present invention is used to adjust a user's circadian rhythms prior to travel to a different time zone. Such adjustment is based on future travel plans 210 provided as an optional input 114 to the method of FIG. 1.

EXAMPLE 2

For purposes of this example, we assume the athlete of Example 1 has an event scheduled for noon the next day and that the athlete has several preparations (Priority Events) that must be considered to properly prepare for and enhance the day's performance. Furthermore, the athlete desires to NOT be awakened on the day of the event during a critical sleep cycle, before the completion of his optimum personal sleep cycle, or in such a way that does not encourage optimum performance.

First, the athlete desires to be awakened with sufficient time to:

1) Eat breakfast;
2) Use the bathroom and shower;
3) Stretch;
4) Meditate;
5) Watch a motivational tape;
6) Call home and talk to parents;
7) Drive to the event;
8) Meet with coach for a final pep talk; and,
9) Engage in final warm up and mental prep for the event.

The athlete notices that not all of the above activities are absolutely necessary and that it would be acceptable to forgo or reduce some pre event activities in exchange for obtaining a optimum personal sleep cycle. The athlete enters event data into the system as Code Sequence 1 based on the following information.

Breakfast will take 15 minutes total to order and eat. Breakfast is not an absolute priority. It would be possible to eat high-energy foods in the car on the way to the event. So the breakfast entry is assigned the code of 01-000-015.

The first number represents the first of the sequence of pre-event priorities. The second and third numbers in the sequence represent absolute and optional time allotments in minutes, respectively. The second number is the absolute time in minutes that must be allowed for the respective activity and the athlete must be awakened, regardless of the quality of sleep, with at least this amount of time to perform this function. If the second number is 0, the activity is optional, and can be omitted entirely if necessary. The third number is an optional time allotment in minutes. Since breakfast is not an absolute priority because the alternative of eating in the car on the way to the event exists, an optional time requirement of 15 minutes is established. If the personal sleep cycles are complete with sufficient time for the optional time, the athlete will be awakened with a budget of 15 minutes to eat; otherwise the athlete will be eating in the car.

The athlete's typical bathroom routine takes about 30 minutes, but only 15 minutes would be absolutely necessary. Therefore, this is assigned a code of 02-015-030. The athlete's initial stretching routine typically takes 15 minutes. The athlete knows that initial stretching is preferable, but in this case not absolutely necessary, so priority is given to sleep. Therefore, this is assigned a code of 03-000-015. Meditating is not an absolute priority and is assigned 04-000-030. Watching a motivational tape is not an absolute priority and is assigned 05-000-030. Calling the parents can be done from the car on the way to the event. It is assigned 06-000-005. Driving to the event is an absolute priority and is assigned 07-015-015. Meeting with coach for a final pep talk is not an absolute priority and is assigned 08-000-010. Final warm up and prep is an absolute priority and is assigned 09-015-015.

At any time prior to the event, the athlete enters the following data into the system.

| 1) Priority Data: | |
| --- | --- |
| Breakfast | 01-000-015 |
| Bath | 02-015-030 |
| Stretch | 03-000-015 |
| Meditate | 04-000-030 |
| Watch Tape | 05-000-030 |
| Call Home | 06-000-005 |
| Drive | 07-015-015 |
| Coach | 08-000-010 |
| Warm up | 09-015-015 |
| | |
| TOTAL | 045-165 |
| 2) Event time: | 01-05-03-1200 (Dec. 5, 2003 at 12 noon) |
| 3) Other Data: | 60 R X1345 Y2 3 15 |

The athlete also knows from previous use of the system which sleep cycle stages is optimum to be awakened during and which are not. In this example the athlete performs best after three complete sleep cycles, and then only after being awakened during phase 2 sleep. Furthermore, the athlete is a heavy sleeper, and can take as much as 15 minutes to wake up after the alarm begins to sound. This information, as well as other information, is included in "Other Data" as follows:

"60" Undercover Temperature

The athlete knows from previous use of the system that his sleep cycles are most consistent when his "undercover" temperature (temperature as taken immediately under the covers) is 60 degrees.

"R" Alarm Data

The athlete's hero is Martin Luther King and he is greatly inspired by King's "I have a dream speech". Excerpts of King's speech were previously recorded into the alarm unit and the alarm unit is set for gradual and repetitive alarm. The system allows the speech excerpts to start playing quietly, then repeat while gradually getting louder until the maximum audio limit is reached, or the alarm is turned off.

"X" Negative Cycle

"X" is followed by numbers 1, 2, 3, 4 and/or 5, representing stages of sleep during which awakening is not preferred. In this example, X1345 indicates that awakening is to be inhibited during stages 1, 3, 4, and 5 of sleep.

"Y" Positive Cycle

"Y" is followed by numbers 1, 2, 3, 4 and/or 5, representing stages of sleep during which awakening is preferred. In this example, Y2 indicates that awakening is preferred during stage 2 sleep.

"3" Optimum REM Cycles

"3" represents the number of REM stages (i.e., sleep cycles) desired.

"15" Waking Period

"15" represents the amount of time in minutes that it might take to awaken the athlete, based on previous use of the system.

The night prior to the event the athlete places a headband, finger slips, or nose bridge on, or a combination thereof, depending on what signals have been determined as necessary in prior use of the system, verifies the alarm settings, and goes to sleep.

The system adds up the total time for the priority data and the 15 minutes allocated for the alarm and stores the Alarm Data and event time. The absolute priority time totals 60 minutes (45 minutes for events plus 15 minutes for the alarm) or one hour, and the optional time totals 180 minutes (165 minutes for events plus 15 minutes for the alarm), or 3 hours. The system subtracts each from 12:00 PM and stores 11:00 AM as the absolute latest wakeup time, and 9:00 AM as the most convenient wakeup time. The system defaults to awakening the athlete at any time that the optimum number of sleep cycles have occurred, which may be before 9:00 AM in this example.

The system monitors the athlete's sleep and records the sleep cycles while continuously referencing the convenient and latest wake up times and the actual time. The system knows other details of the athletes typical sleep patterns from analyzing the Historical Data.

During the night, the athlete is awakened by the sound of a siren during a deep sleep stage, and subsequently has a hard time going back to sleep because of worries associated with the event. This disruption in the sleep cycle and subsequent difficulty in falling back asleep has delayed completion of the athlete's third REM stage. Therefore adjustment must be made to the alarm time.

At 9:00 AM the system notes that third REM stage has not been completed. It further notes that the athlete is in a phase 3 sleep stage, only 2 stages away from the third REM stage. According to the user historical data 206, each REM stage gets longer as the night progresses. The system uses an average based on similar sleep scenarios to estimate that the last REM stage will start in 15 minutes and last for 90 minutes. The system further estimates, based on user historical data 206, that it will then take an additional 15 minutes to get into a stage 2 sleep cycle, which is the preferred stage for awakening. The system calculates a delay of 120 minutes, thus delaying the alarm time to 11:00 AM. The system checks to see if this is later than the latest alarm time and discovers that it coincides. The system continues to monitor the athlete, since the estimate indicates that the desired number of sleep cycles can be completed before the latest possible awakening time.

The system notes that the athlete is getting through stages three and four much faster than usual and that the athlete enters the third REM stage in only 5 minutes instead of the previously estimated 15 minutes. The system begins to monitor the third REM stage. During the third REM stage the system notes that the temperature under the blanket has fallen to under 60 degrees and therefore sends a signal to the electric blanket control to increase the temperature until 60 degrees is reached. By doing so the third REM stage is not interrupted and further turns out to be shorter than the average and totals only 40 minutes. The historical data confirms that this is long enough to be considered part of a full optimum personal sleep cycle. The system then monitors the athlete going through the fourth stage 1 sleep phase in 5 minutes and as the athlete enters the fourth stage 2 sleep phase the awakening condition is met, and at 9:50 AM King's speech begins to play.

The athlete wakes up 15 minutes later and the system display reads:

| Time: | 10:05 AM | |
|---|---|---|
| Prep: | 1 hrs 55 minutes. | |
| Priority Scale: | linear (50 minutes/7) | |
| Schedule: | | |
| 9:50-10:05 | Sound alarm | |
| 10:05-10:12 | Breakfast | 15 – 8 = 7 |
| 10:12-10:34 | Bathroom | 30 – 8 = 22 |
| 10:34-10:41 | Stretch | 15 – 8 = 7 |
| 10:41-11:04 | Meditate | 30 – 7 = 23 |
| 11:04-11:27 | Watch Tape | 30 – 7 = 23 |
| | NO CALL | 5 – 7 = 0 |
| 11:27-11:42 | Drive | 15 |
| 11:42-11:45 | Coach Pep | 10 – 7 = 3 |
| 11:45-12:00 | Final Prep | 15 |
| 12:00 | Event start | |

In this example, 50 minutes had to be subtracted from the total optional event time. Since seven of the nine scheduled events have optional time allocations, reducing six of these optional time allocations by 7 minutes and one by 8 minutes will distribute the schedule reduction equally among the optional activities. In this example, the phone call is eliminated from the schedule, since it was only allotted 5 optional minutes. Also, two additional minutes are taken away from other activities since eliminating the phone call only frees up 5 minutes. This rescheduling is preferably done automatically by processor 304. Of course, this is only one example of how absolute and optional time requirements for event priority data 204 can be used to automatically provide a schedule 110 to a user.

It will be clear to one skilled in the art that the above embodiments may be altered in many ways without departing from the scope of the invention. For instance, the analysis of monitored signals and comparison with historical data could be performed remotely. Furthermore the system could be a small package with onboard processing, memory and data acquisition. The storage could also be performed onboard or off-line. Yet another variation is that the monitoring could be performed continuously or at discrete time intervals which have sufficient time resolution for monitoring/counting of sleep cycles.

What is claimed is:

1. A method for awakening a user from sleep, the method comprising:
   a) monitoring sleep cycles of said user;
   b) counting said sleep cycles to provide a sleep cycle count;
   c) inputting one or more sleep cycle counts to a decision algorithm;
   d) inputting historical user data to the algorithm;
   e) selecting a time according to a decision algorithm using said historical user data and sleep cycle count as an input to said algorithm; and
   f) awakening said user at said selected time.

2. The method of claim 1, further comprising providing event priority data for a following day as an input to said decision algorithm.

3. The method of claim 2, further comprising providing a schedule to said user after said awakening based on said event priority data and on said selected time.

4. The method of claim 2, further comprising providing absolute time requirements and optional time requirements as event priority data.

5. The method of claim 1, further comprising providing preferences of said user as an input to said decision algorithm.

6. The method of claim 1, further comprising providing information on future travel of said user to a different time zone as an input to said decision algorithm.

7. The method of claim 6, further comprising providing a nominal awakening time adjusted from day to day prior to said travel.

8. The method of claim 1, further comprising providing a nominal awakening time as an input to said decision algorithm.

9. The method of claim 1, further comprising modifying said sleep cycles.

10. The method of claim 9, further comprising altering one or more environmental conditions comprising ambient temperature, ambient light level and ambient sound level to modify said sleep cycles.

11. The method of claim 1, further comprising providing an indication as to whether or not sufficient rest was obtained.

12. A system for awakening a user from sleep, the system comprising:
   a) a monitor for monitoring sleep cycles of said user;
   b) a historical user data base;
   c) a processor for counting said sleep cycles responsive to input from said monitor to provide a sleep cycle count and input from the user historical data base for selecting a time according to a decision algorithm including said sleep cycle count and historical data as an input; and
   c) an alarm for awakening said user at said selected time.

13. The system of claim 12, further comprising a modifier for adjusting said sleep cycles.

14. The system of claim 13, said modifier further comprising one or more devices for controlling ambient temperature, ambient light level or ambient sound level.

15. The system of claim 12, further comprising the processor responsive to event priority data for a following day as an input to said decision algorithm.

16. The system of claim 15, having said processor provide at least one schedule to said user after said awakening based on said event priority data and on said selected time.

17. The system of claim 15, further comprising the processor responsive to absolute and optional time requirements as priority data inputs.

18. A method for regulating sleep cycles of a human comprising:
   a) collecting the human's historical biological data;
   b) analyzing the human's historical biological data to determine historical sleep cycles;
   c) measuring current sleep cycles;
   d) calculating an optimal awakening time based on historical and current sleep cycles; and
   f) awakening the human to maximize sleep cycles.

19. The method of claim 18 further comprising adjusting the awakening for external events.

20. The method of claim 18 further comprising adjusting the awakening in response to the human's optimum personal sleep cycle.

21. The method of claim 18 further comprising adjusting the human's environment while sleeping based on historical and current sleep cycle input and historical biological data.

22. The method of claim 18 further comprising adjusting the awakening to accommodate scheduled events.

23. The method of claim 18 further comprising using selected stimulus to awaken.

24. A method for regulating sleep cycles of a human comprising:
- collecting the human's historical and current biological data;
- analyzing the human's biological data to determine sleep cycles;
- determining awakening time using an algorithm to collect and measure biological data and optional inputs; and
- awakening the human to maximize sleep cycles.

25. A system predicting optimum awakening time, comprising:
- an algorithm using recursive analytics;
- a data base of historic user sleep cycles and correlated biologic functions;
- input of event priority data to the algorithm for a post sleep cycle;
- a monitor for current sleep cycles and biologic functions of the user;
- a data collector for measuring said sleep cycles and collecting biologic data responsive to input from said monitor and providing data to the algorithm;
- optimization of the predicted awakening time based on recursive analysis of current and historic sleep cycles and biologic data by the recursive analytics; and
- an alarm for awakening said user at said selected time.

26. The system of claim 25, said system providing at least one schedule to the user after awakening based on said event priority data and on the selected time.

27. The system of claim 25 further comprising adjusting the ambient sleep condition of the user in response to output from the algorithm.

* * * * *